(12) United States Patent
Florent et al.

(10) Patent No.: US 12,419,600 B2
(45) Date of Patent: Sep. 23, 2025

(54) SUBTRACTION IMAGING

(71) Applicant: KONINKLIJKE PHILIPS N.V., Eindhoven (NL)

(72) Inventors: Raoul Florent, Ville d'Avray (FR); Claire Levrier, Rueil-Malmaison (FR); Christian Haase, Hamburg (DE); Haithem Boussaid, Chatenay Malabry (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 191 days.

(21) Appl. No.: 18/282,595

(22) PCT Filed: Mar. 14, 2022

(86) PCT No.: PCT/EP2022/056447
§ 371 (c)(1),
(2) Date: Sep. 18, 2023

(87) PCT Pub. No.: WO2022/200089
PCT Pub. Date: Sep. 29, 2022

(65) Prior Publication Data
US 2024/0164733 A1    May 23, 2024

(30) Foreign Application Priority Data
Mar. 23, 2021 (EP) .................... 21290018

(51) Int. Cl.
*G06T 7/00* (2017.01)
*A61B 6/00* (2006.01)
*A61B 6/50* (2024.01)

(52) U.S. Cl.
CPC .............. *A61B 6/504* (2013.01); *A61B 6/481* (2013.01); *A61B 6/5258* (2013.01); *G06T 7/00* (2013.01); *G06T 2207/10116* (2013.01)

(58) Field of Classification Search
CPC ......... A61B 6/504; A61B 6/503; A61B 6/502; A61B 6/5258; A61B 6/5205;
(Continued)

(56) References Cited

U.S. PATENT DOCUMENTS 7,409,078 B2    8/2008    Pescatore et al.
7,432,924 B2   10/2008    Ohishi
(Continued)

FOREIGN PATENT DOCUMENTS

EP       1510972 A2      3/2005
JP     2015211914 A     11/2015
(Continued)

OTHER PUBLICATIONS

Van Tran et al., "Flexible Mask Subtraction for Digital Angiography", IEEE Transactions on Medical Imaging, IEEE Service Center, Piscataway, NJ, US, vol. 11, No. 3, Sep. 1, 1992.
(Continued)

*Primary Examiner* — Don K Wong

(57) ABSTRACT

The present invention relates to subtraction imaging. In order provide further improved accuracy of masking images, a device (10) for digital subtraction imaging is provided comprising an image data input (12), a data processor (14) and an output interface (16). 3D image data (22) of a region of interest of an object is received that comprises a 3D representation of the object based on a reconstruction from a plurality of 2D projection images. Further, a 2D live X-ray image (24) of the region of interest is received. The 3D image data and the 2D live X-ray image are registered, wherein a matching pose of the 3D image data corresponding to the 2D live X-ray image is determined. A digitally reconstructed radiography is computed from the 3D image data based on the determined matching pose to generate a 2D mask image. For the 2D mask image, current data related (Continued)

to the 2D live X-ray image is used to achieve an adapted 2D mask image, wherein the data related to 10 the 2D live X-ray image comprises 2D live acquisition parameters and/or data of the 2D live X-ray image. The generated adapted 2D mask is subtracted image from the 2D live X-ray image a digital image highlighting changes in the region of interest is provided.

15 Claims, 4 Drawing Sheets

(58) Field of Classification Search
CPC . A61B 6/5211; A61B 2576/023; A61B 6/466; A61B 2017/00703; A61B 2090/367; A61B 2090/376; A61B 5/0044; G06T 2207/10121; G06T 2211/404; G06T 2207/30048; G06T 2207/20224; G06T 7/38; G06T 7/00; G06T 11/00
See application file for complete search history.

(56) References Cited

U.S. PATENT DOCUMENTS

| | | | |
|---|---|---|---|
| 9,367,904 B2 | 6/2016 | Weese et al. | |
| 10,140,734 B2 | 11/2018 | Chen | |
| 10,258,301 B2 | 4/2019 | Rouet et al. | |
| 10,682,112 B2 | 6/2020 | Pizaine et al. | |
| 2010/0172474 A1 | 7/2010 | Vogt et al. | |
| 2017/0124708 A1* | 5/2017 | Baumgart | A61B 6/5205 |

FOREIGN PATENT DOCUMENTS

| | | | |
|---|---|---|---|
| JP | 2019076192 A | 5/2019 |
| WO | 2016110420 A1 | 7/2016 |
| WO | 2020174284 A1 | 9/2020 |

OTHER PUBLICATIONS

Meijering et al., "Retrospective Motion Correction in Digital Subtraction Angiography: A Review", IEEE Transactions on Medical Imaging, IEEE Service Center, Piscataway, NJ, US, vol. 18, No. 1, Jan. 1, 1999, pp. 2-21.

Copeland et al. "Spatio-Temporal Data Fusion for 3D+T Image Reconstruction in Cerebral Angiography" IEEE Transactions on Medical Imaging 29.6 (2010): 1238-1251. Web. Apr. 5, 2012. © 2010 Institute of Electrical and Electronics Engineers.

International Search report and Written Opinion of PCT/EP2022/056447, dated Jul. 11, 2022.

* cited by examiner

SUBTRACTION IMAGING

CROSS-REFERENCE TO PRIOR APPLICATIONS

This application is the U.S. National Phase application under 35 U.S.C. § 371 of International Application No. PCT/EP2022/056447, filed on Mar. 14, 2022, which claims the benefit of European Patent Application No. 21290018.7, filed on Mar. 23, 2021. These applications are hereby incorporated by reference herein.

FIELD OF THE INVENTION

The present invention relates to subtraction imaging, and relates in particular to a device for digital subtraction imaging, to an imaging system for digital subtraction imaging and to a method for digital subtraction imaging.

BACKGROUND OF THE INVENTION

X-ray imaging is used for visualizing regions of interest within an object. However, X-ray based imaging techniques, e.g. fluoroscopy, computed tomography, etc., are limited regarding blood vessels, because the X-ray attenuation properties of blood and adjacent tissues are very similar. In order to visualize vasculature, radio-opaque contrast media can be injected into blood vessels to increase the X-ray attenuation within the blood vessels. For clearer visualization of blood vessels without distraction from surrounding tissues, which can reduce the visibility of blood vessels, Digital Subtracted Angiography (DSA) images are computed by subtracting a pre-contrast mask image from the contrast-enhanced images of the same structure. However, due to patient motion, the alignment of the mask image (typically non-injected) and of the live image (typically filled with contrast agent) is not perfect. The net effect is a sub-optimal subtraction, with the presence of what is usually referred to as motion artefacts. U.S. Ser. No. 10/682,112 B2 relates to suppression of independent movements in a series of 3D X-ray fluoroscopy images using a 3D pre-operative volume and describes that digitally reconstructed radiograph images of a 3D-2D registration of the (preoperative) three-dimensional volume of the structures to be removed from the X-ray images is generated. This includes the projection of the structures onto the correct viewing plane as well as a registration thereof. The digitally reconstructed radiograph images are subtracted from the X-ray images for generating structure-suppressed fluoroscopy images free of undesired/interfering motion of the suppressed structures. However, it has been shown that artefacts can still occur.

SUMMARY OF THE INVENTION

There may thus be a need for further improved accuracy of masking images.

The object of the present invention is solved by the subject-matter of the independent claims; further embodiments are incorporated in the dependent claims. It should be noted that the following described aspects of the invention apply also for the device for digital subtraction imaging, for the imaging system for digital subtraction imaging and for the method for digital subtraction imaging.

According to the present invention, a device for digital subtraction imaging is provided. The device comprises an image data input, a data processor and an output interface. The image data input is configured to receive 3D image data of a region of interest of an object, the 3D image data comprising a 3D representation of the object that is based on a reconstruction from a plurality of 2D projection images of the region of interest. The image data input is also configured to receive a 2D live X-ray image of the region of interest. Further, the data processor is configured to register the 3D image data and the 2D live X-ray image, wherein a matching pose of the 3D image data corresponding to the 2D live X-ray image is determined. The data processor is also configured to compute a digitally reconstructed radiography from the 3D image data based on the determined matching pose to generate a 2D mask image. The data processor is also configured to use, for the generating of the 2D mask image, current data related to the 2D live X-ray image to achieve an adapted 2D mask image. The data related to the 2D live X-ray image comprises at least one of the group of 2D live acquisition parameters and data of the 2D live X-ray image. The data processor is further configured to subtract the generated adapted 2D mask image from the 2D live X-ray image. Still further, the output interface is configured to provide a digital image highlighting changes in the region of interest.

As an effect, the adaptation compensates that the digital digitally reconstructed radiograph (DRR) images and the live images originate from different data and formation processes. The adaptation reduces artefacts in the subtraction images and thus provides visualization of the current situation in form of the subtraction images with improved accuracy.

According to an example, the image data input is configured to receive an angiographic contrast injected 2D live X-ray image of the region of interest as the 2D live X-ray image. The data processor is configured to subtract the generated adapted 2D mask image from the angiographic contrast injected 2D live X-ray image. The output interface is configured to provide a digital subtraction angiography representing a vascular structure in the region of interest.

According to an example, for achieving the adapted 2D mask image, the image data input is configured to receive the projection data of the region of interest comprising the plurality of the 2D projection images. The image data input is also configured to receive 2D data characteristics from an acquisition of the 2D live X-ray image. Further, the data processor is configured to adapt, based on the 2D data characteristics, the reconstruction of the projection data of the region of interest to generate adapted 3D image data that comprises an adapted 3D representation of the object. The data processor is also configured to use the adapted 3D image data for the computation of the digitally reconstructed radiography.

According to an option, the data processor is configured to use the adapted 3D image data also for the registration.

According to an example, for achieving the adapted 2D mask image, the image data input is configured to receive 2D data characteristics from an acquisition of the 2D live X-ray image. The data processor is configured to adapt, based on the 2D data characteristics, the computation of the digitally reconstructed radiography from the 3D image data to generate an adapted 2D mask image.

According to an example, the 2D data characteristics are based on i) 2D live acquisition parameters comprising at least one of the group of spectrum, resolution and X-ray imaging energy. In addition or alternatively, the 2D data characteristics are based on ii) image data of the 2D live X-ray image comprising at least one of the group of resolution and contrast.

According to an example, for the 3D image data, the adapted reconstruction comprises reconstructed attenuation values that correspond to a predetermined mean photon energy which is expected to be used for the 2D live X-ray image.

According to an option, the data processor is configured to segment the 3D image segmented into bone and soft tissue type regions so that each tissue type has individually adjusted attenuation values for the expected photon energy.

According to another option, the data processor is configured to apply different spectrum-related factors for the digitally reconstructed radiography.

According to a further option, the 3D image data is vessel-les.

According to an example, the data processor is configured to estimate a pose of the object in the 2D live X-ray image. For the registration of the 3D image data and the 2D live X-ray image, the data processor is configured to align the 3D representation of the object of the 3D image data to the estimated pose. In addition or alternatively, for the reconstruction of the projection data of the region of interest, the data processor is configured to consider the estimated pose for the reconstruction.

According to an example, the data processor is configured to provide a 2D scatter estimation using the 2D live X-ray image as input or a 3D scatter estimation. The data processor is configured to add a scatter signal to the computed digitally reconstructed radiography.

According to an example, as correction for the reconstruction of the 3D image data, the data processor is configured to provide i) a virtual heel effect correction. In addition or alternatively, the data processor is configured to provide ii) a virtual inverse detector gain correction.

According to an example, a display is provided to present the digital representing the vascular structure in the region of interest.

According to the present invention, also an imaging system for digital subtraction imaging is provided. The system comprises an X-ray imaging device with an X-ray source and an X-ray detector and a device for digital subtraction imaging according to one of the preceding examples. The X-ray imaging device is configured to generate the 2D live X-ray image.

According to the present invention, also a method for digital subtraction imaging is provided. The method comprising the following steps: receiving 3D image data of a region of interest of an object, wherein the 3D image data comprises a 3D representation of the object that is based on a reconstruction from a plurality of 2D projection images of the region of interest; receiving a 2D live X-ray image of the region of interest; registering the 3D image data and the 2D live X-ray image, wherein a matching pose of the 3D image data corresponding to the 2D live X-ray image is determined; computing a digitally reconstructed radiography from the 3D image data based on the determined matching pose to generate a 2D mask image. For the generating of the 2D mask image, current data related to the 2D live X-ray image is used to achieve an adapted 2D mask image, wherein the data related to the 2D live X-ray image comprises at least one of the group of 2D live acquisition parameters and data of the 2D live X-ray image. It is further provided the steps of subtracting the generated adapted 2D mask image from the 2D live X-ray image; and providing a digital image highlighting changes in the region of interest.

A field of application is neurology, and in particular neuro-interventions. Another suitable field are spine-related interventions.

According to an aspect, the 3D-generated mask images are adapted to the live images. For that, in an example, the live image characteristics are extracted and introduced in the reconstruction process so as to adapt the generated 3D volume to the live image. Alternatively or additionally, the matching digitally reconstructed radiograph are adapted to the live image content and characteristics. This (potentially double) mechanism targets at least spectrum, scatter and resolution adaptation.

According to an aspect, two main sources of adaptations are provided. In a first option, one adaptation is provided at 3D reconstruction time, i.e. during the 3D reconstructing, and a second option, in addition or alternatively, one adaptation is provided at digitally reconstructed radiography generation time, i.e. during computing the digitally reconstructed radiography. According to an aspect, these two sources, though coupled when used in conjunction, can also be used independently, e.g. one without the presence of the other.

The adaptation is suitable in particular for use in interventional X-ray imaging systems, e.g. fixed and mobile imaging systems, for various X-ray based procedures that use contrast enhanced imaging comprising for example endovascular procedures, e.g. stenosis detection, aneurysm embolization, neuro stroke treatment, etc., but not limited to these.

According to another aspect, as an option, the adaptation of the mask image generation to the current live situation is provided to other subtractive imaging techniques, in particular to roadmapping or device visualization. For instance, during the steering of a device in a vascular system, the fluoroscopic images are visualized after subtraction in order to remove the background content, and only leave the device visible. In another example, the footprint of vessels acquired at a previous intervention time, are superimposed during device manipulation for guidance purposes. It is noted that any motion occurring between the two steps of the imaging technique (previous versus live instants) would degrade the subtraction process. The adaptation is thus also suitable for those cases.

According to a further aspect, a device for digital subtraction imaging is provided comprising an image data input, a data processor and an output interface. 3D image data of a region of interest of an object is received that comprises a 3D representation of the object based on a reconstruction from a plurality of 2D projection images. Further, a 2D live X-ray image of the region of interest is received. The 3D image data and the 2D live X-ray image are registered, wherein a matching pose of the 3D image data corresponding to the 2D live X-ray image is determined. A digitally reconstructed radiography is computed from the 3D image data based on the determined matching pose to generate a 2D mask image. For the 2D mask image, current data related to the 2D live X-ray image is used to achieve an adapted 2D mask image, wherein the data related to the 2D live X-ray image comprises 2D live acquisition parameters and/or data of the 2D live X-ray image. The generated adapted 2D mask is subtracted image from the 2D live X-ray image a digital image highlighting changes in the region of interest is provided.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
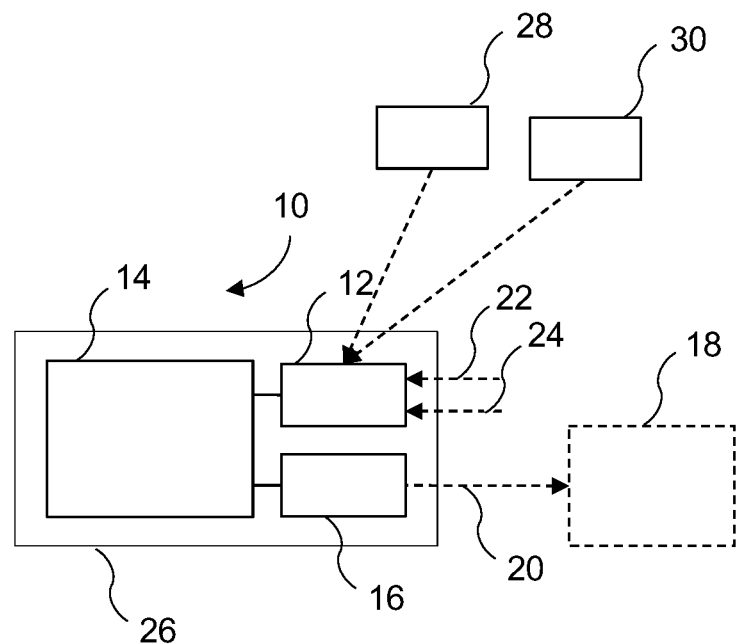
FIG. 1 schematically shows an example of a device for digital subtraction imaging.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

The term "subject" may also be referred to as individual. The "subject" may further also be referred to as patient, although it is noted that this term does not indicate whether any illness or disease is actually present with the subject.

FIG. 1 schematically shows an example of a device 10 for digital subtraction imaging. The device 10 comprises an image data input 12, a data processor 14 and an output interface 16.

As an option, also a display 18 is provided to present a digital image representing a vascular structure in a region of interest of a subject. A dotted arrow 20 indicates a data connection providing the data for the display 18.

The image data input 12 is configured to receive 3D image data 22 of a region of interest of an object, the 3D image data comprising a 3D representation of the object that is based on a reconstruction from a plurality of 2D projection images of the region of interest. The image data input 12 is also configured to receive a 2D live X-ray image 24 of the region of interest. The data processor 14 is configured to register the 3D image data and the 2D live X-ray image, wherein a matching pose of the 3D image data corresponding to the 2D live X-ray image is determined. The data processor 14 is also configured to compute a digitally reconstructed radiography from the 3D image data based on the determined matching pose to generate a 2D mask image. The data processor 14 is further configured to use, for the generating of the 2D mask image, current data related to the 2D live X-ray image to achieve an adapted 2D mask image, wherein the data related to the 2D live X-ray image comprises at least one of the group of 2D live acquisition parameters and data of the 2D live X-ray image. The data processor 14 is furthermore configured to subtract the generated adapted 2D mask image from the 2D live X-ray image.

The output 16 interface is configured to provide a digital image, indicated by the arrow 20, the digital image highlighting changes in the region of interest.

A surrounding frame 26 indicates an option that the image data input 12, the data processor 14 and the output interface 16 can be arranged in a common structure like a housing. However, they can also be provided as separate components.

Figure 2:
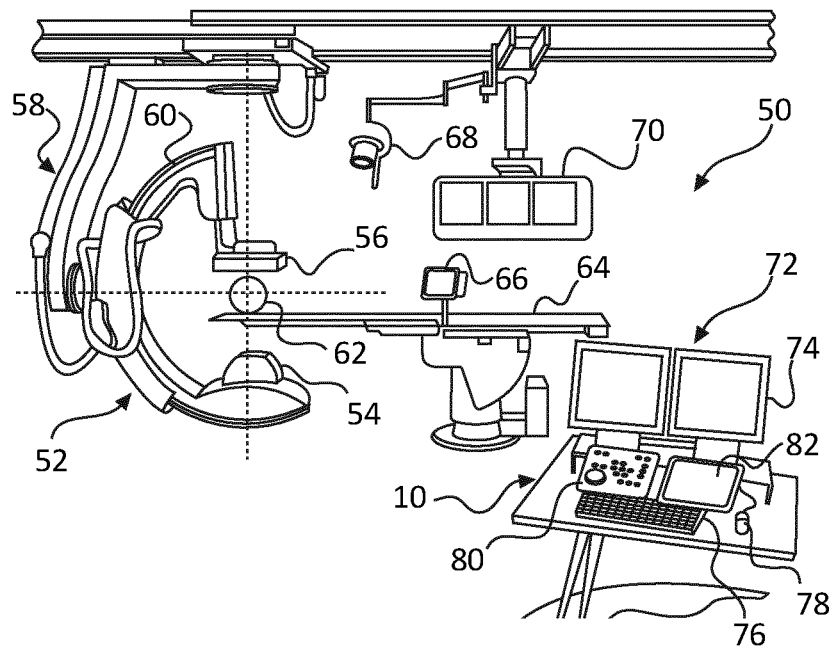
FIG. 2 shows an example of an imaging system for digital subtraction imaging.

FIG. 2 shows an example of an imaging system 50 for digital subtraction imaging. The system 50 comprises an X-ray imaging device 52 with an X-ray source 54 and an X-ray detector 56. Further, an example of the device 10 for digital subtraction imaging according to one of the preceding and following examples is provided. The X-ray imaging device 52 is configured to generate the 2D live X-ray image.

The X-ray imaging device 52 comprises a support structure 58 which is movably suspended from a ceiling structure. In another option, a mobile X-ray imaging device is provided, or a fixed but movable system supported on the floor. In the example shown, a movable C-arm 60 is provided which carries the X-ray source 54 and the X-ray detector 56. An object 62 with the region of interest is indicated, the object being arranged on an adjustable subject support table 64. A bedside controller 66 is also indicated. Above, lighting equipment 68 is provided and display equipment 70.

The example of the device 10 for digital subtraction imaging is provided in the context of a work station or console 72 shown in the foreground. The console 72 comprises displays 74, a keyboard 76 and a mouse 78. Further, a control console 80 and a graphical tablet 82 are indicated.

The imaging system for digital subtraction imaging is also referred to as imaging system for digital subtraction angiography.

In an option, the X-ray imaging device is also configured to generate the plurality of 2D projection images for the reconstruction of the 3D image data.

Figure 3:
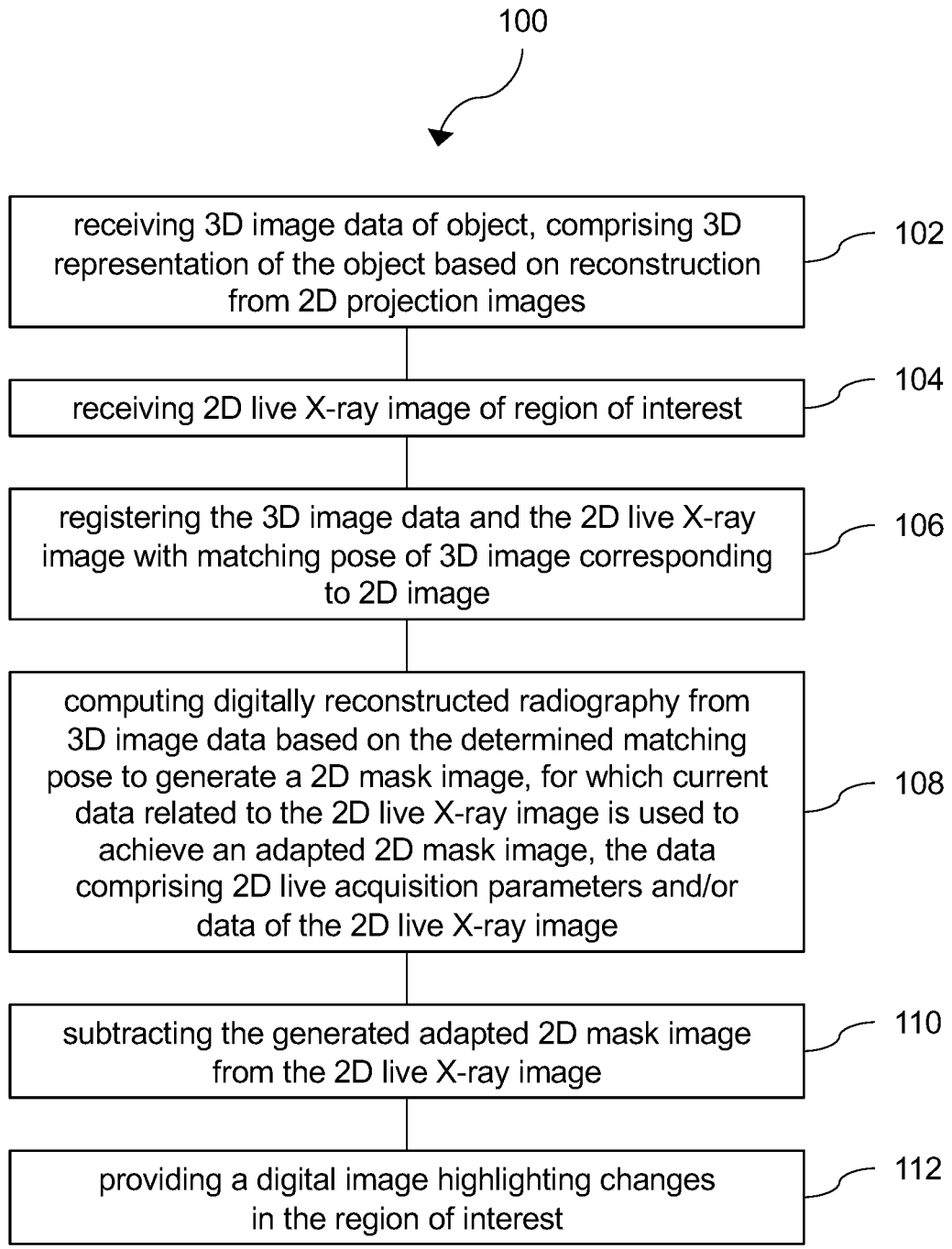
FIG. 3 shows basic steps of an example of a method for digital subtraction imaging.

FIG. 3 shows basic steps of an example of a method 100 for digital subtraction imaging. The method 100 comprises the following steps:

In a first step 102, 3D image data of a region of interest of an object is received. The 3D image data comprises a 3D representation of the object that is based on a reconstruction from a plurality of 2D projection images of the region of interest.

In a second step 104, a 2D live X-ray image of the region of interest is received.

In a third step 106, the 3D image data and the 2D live X-ray image are registered. A matching pose of the 3D image data corresponding to the 2D live X-ray image is determined.

In a fourth step 108, a digitally reconstructed radiography is computed from the 3D image data based on the determined matching pose to generate a 2D mask image. For the generating of the 2D mask image, current data related to the 2D live X-ray image is used to achieve an adapted 2D mask image, wherein the data related to the 2D live X-ray image comprises at least one of the group of 2D live acquisition parameters and data of the 2D live X-ray image.

In a fifth step 110, the generated adapted 2D mask image is subtracted from the 2D live X-ray image.

In a sixth step 112, a digital image highlighting changes in the region of interest is provided.

In an option, the 2D live X-ray image is provided as an angiographic contrast injected 2D live X-ray image of the region of interest. For the subtraction, the generated adapted 2D mask image is subtracted from the angiographic contrast injected 2D live X-ray image. For the provision of the digital image, a digital subtraction angiography is provided representing a vascular structure in the region of interest.

The method for digital subtraction imaging can also be referred to as method for digital subtraction angiography.

In an example of the method, the plurality of the 2D projection images is provided as a set of images forming a scan of images. In an example, a plurality of scans, i.e. two or more sets of images each comprising a plurality of the 2D projection images are provided.

The computed digitally reconstructed radiography is an approximation of the 2D image that the X-ray system would generate when imaging the 3D volume under the provided pose.

The 3D image data is also referred to as 3D reconstruction data. The 3D image data provides projection data for the generation of a 2D projection image, i.e. an image like an X-ray image, but in this case a virtual projection of the 3D image data on a virtual detector plane. Therefore, the 3D image data is also referred to as projection data.

The 2D live X-ray image is also referred to as 2D live data.

The 3D image data is also referred to as 3D image data set.

The 3D image data is provided as 3D reconstruction data, i.e. as a 3D data set representing the area of interest.

In an example, the 3D reconstruction data is a 3D data set representing the area of interest. For instance, in a neuro intervention, this could be a 3D representation of the head, reconstructed from a rotational scan performed without contrast injection and producing the so-called projection data. In this case, the 3D data represent the bone and soft-tissue head anatomy, but without the vascular part (invisible to X-ray). Without contrast injection these can not be distinguished from surrounding soft tissue using X-ray.

In another scenario, a 3D scan is provided with contrasted vessels and a 2D live (fluoro) data is provided without contrast agent. This is used to create a virtual vessel road map on the fluoro data and allows navigation without further contrast injection.

The 2D live X-ray image is provided, i.e. acquired, by an angiographic acquisition.

In an example, the 2D projections scans are provided as a plurality of scans of a rotational C-arm scan. In another example, the 2D projections scans are provided as plurality of scans of a CT scan.

In a variation, the C-arm scan is provided without contrast agent.

In an example, the current data related to the 2D live X-ray image comprises 2D data characteristics. In an example, predetermined essential characteristics of the 2D data such as the X-ray spectrum that is used to produce the live image or its resolution are gathered. The 2D data characteristics can be derived from acquisition parameters from the system or directly from the live image content itself.

In an example, the 2D live X-ray image is provided as an angiographic contrast injected 2D live X-ray image of the region of interest.

In another example, the 2D live X-ray image is provided as a fluoro image without contrast, but with a device inserted. For example, the subtraction can then help to highlight the device during intravascular navigation.

Referring back to FIG. 1, in an example of the device, not shown in detail, the image data input 12 is configured to receive an angiographic contrast injected 2D live X-ray image of the region of interest as the 2D live X-ray image. The data processor 14 is configured to subtract the generated adapted 2D mask image from the angiographic contrast injected 2D live X-ray image. The output interface 16 is configured to provide a digital subtraction angiography representing a vascular structure in the region of interest. The device 10 for digital subtraction imaging can also be referred to as device for digital subtraction angiography.

In an example of the device, indicated as an option in FIG. 1, for achieving the adapted 2D mask image, the image data input 12 is configured to receive the projection data of the region of interest comprising the plurality of the 2D projection images. The image data input 12 is also configured to receive 2D data characteristics 28 from an acquisition of the 2D live X-ray image. The data processor 14 is configured to adapt, based on the 2D data characteristics 28, the reconstruction of the projection data of the region of interest to generate adapted 3D image data that comprises an adapted 3D representation of the object. The data processor 14 is further configured to use the adapted 3D image data for the computation of the digitally reconstructed radiography.

In an option, the data processor 14 is configured to use the adapted 3D image data also for the registration.

In an example, an adapted 3D reconstruction is provided. This allows for specific adaptations to produce a volume that will be more capable of delivering 2D-live-compatible digitally reconstructed radiographies. This results in compatibility with a given volume of the targeted anatomy through the adapted digitally reconstructed radiography idea.

In an example of the device, indicated as an additional or alternative option in FIG. 1, for achieving the adapted 2D mask image, the image data input 12 is configured to receive 2D data characteristics 30 from an acquisition of the 2D live X-ray image. The data processor 14 is configured to adapt, based on the 2D data characteristics 30, the computation of the digitally reconstructed radiography from the 3D image data to generate an adapted 2D mask image.

In an example, for an adapted DRR generation, the digitally reconstructed radiography is adaptable to the live image content and characteristics. For instance, a 3D or a 2D scatter estimator is used to add a scatter signal to the digitally reconstructed radiography. The 2D approach will use the angiographic image as input rather than the DRR (digitally reconstructed radiography) or the 3D reconstruction, since it may contain scattering structures that are not in the field of view of the 3D reconstructed image, e.g. the object support, also referred to as patient table.

Further improvements that can make the digitally reconstructed radiography and the angiography more consistent is a virtual heel effect and a virtual inverse detector gain correction. For both effects, calibration data from the image reconstruction pipeline is used. But in an example, the digitally reconstructed radiography process also contains spectrum adaptation or resolution recovery as post processing. In an example, the adapted digitally reconstructed radiography calculation receives both the live image and its characteristics as input.

In an option, for achieving the adapted 2D mask image, the reconstruction of the projection data of the region of interest and the computation of the digitally reconstructed radiography are adapted based on the 2D data characteristics.

In an example of the device, not shown in detail, the 2D data characteristics are based on i) 2D live acquisition parameters comprising at least one of the group of spectrum, resolution and X-ray imaging energy. Alternatively, or in addition, the 2D data characteristics are based on ii) image data of the 2D live X-ray image comprising at least one of the group of resolution and contrast. The adaptation using the 2D data characteristics provides a calibration-type alignment between the data acquisition (of the plurality of 2D images) for the 3D data and the data acquisition for the 2D live data.

During the adapted 3D reconstruction, the characteristics of the 2D live data, such as its spectrum are used in an example to improve 3D/2D compatibility. As an example, compatibility of the 3D reconstruction is improved by using specific beam hardening correction methods during the reconstruction of the 3D attenuation values. It may be beneficial, for example, if the reconstructed attenuation values correspond to the mean photon energy that is expected to be used by the 2D live data acquisition. This mean photon energy may be different than the mean photon energy during the rotational acquisition that is used for 3D reconstruction, e.g. since the X-ray spectra used to produce the 3D and the 2D data may be different.

For this purpose, the 3D image may further be segmented into a bone and a soft tissue region by using e.g. a threshold or model based segmentation so that each tissue type has individually adjusted attenuation values for the expected photon energy. As an effect, the X-ray spectrum discrepancy between the projected data and the live data is addressed.

In further examples, other adaptations of the 3D reconstruction are provided such as scatter correction (the scatter effects are removed at reconstruction time) and spatial resolution discrepancy.

In an example, a dual energy or spectral 3D acquisition is provided and one or multiple reconstructions for a specific energy and or material types are created and combined to a final adapted 3D image.

In an example, if the projection data does not permit an ideal 3D reconstruction resolution to match the 2D live data, a neural network based super resolution method is used to further improve the 3D image resolution.

In an example of the device, not shown in detail, for the 3D image data, the adapted reconstruction comprises reconstructed attenuation values that correspond to a predetermined mean photon energy that is expected to be used for the 2D live X-ray image.

Further, as an option, the data processor 14 is configured to segment the 3D image segmented into bone and soft tissue type regions so that each tissue type has individually adjusted attenuation values for the expected photon energy.

Furthermore, as another option, alternatively or in addition, the data processor 14 is configured to apply different spectrum-related factors for the digitally reconstructed radiography.

Still furthermore, as another option, alternatively or in addition, the 3D image data is vessel-les.

As a result, for the virtual projecting in 2D, the 3D image data is provided as adapted 3D image data, which is optimized for the digital reconstruction to generate the digitally reconstructed radiography. The adapted 3D image data may be less suitable for 3D viewing purposes, compared to the standard 3D reconstruction, but improved in view of creating a mask image.

The mean photon energy will typically be different than the mean photon energy during the rotational acquisition that is used for (since X-ray spectra used to produce the 3D and the 2D data are usually different).

In an option, for a segmentation, a threshold- or model-based segmentation is provided.

In an example, the predetermined mean photon energy is provided instead of the beam hardening correction.

In an example, for the reconstruction of the projection data of the region of interest, an adapted reconstruction is provided that comprises beam hardening correction during the reconstruction. The 3D image data is separated into at least two different absorption rate material types. For the digitally reconstructed radiography, different spectrum-related factors are applied. The 3D image data is vessel-less. The term "vessel-less" refers to a 2D image or 3D image data in which vessels of a vascular structure cannot be identified based on the image. The 3D image is thus provided without identifiable vessels.

For example, a first absorption rate material is assigned to portions representing bones and a second absorption rate material is assigned to portions representing tissue.

In an example, the 3D image data is based on contrast injected X-ray images. The image portions showing contrast are removed for the volume generation.

As an example, a contrast filled vessel, or a removable medical device, or an external object like one or several ECG cables may be removed from the 3D data if they are not present in the 2D live data and are not of interest for a specific application.

The beam hardening is an example of specific adaptations that are provided to produce a volume that is more capable of delivering 2D-live-compatible digitally reconstructed radiographies.

In an example of the device, not shown in detail, the data processor 14 is configured to estimate a pose of the object in the 2D live X-ray image. For the registration of the 3D image data and the 2D live X-ray image, the data processor 14 is configured to align the 3D representation of the object of the 3D image data to the estimated pose. Alternatively or in addition, for the reconstruction of the projection data of the region of interest, the data processor 14 is configured to consider the estimated pose for the reconstruction.

The term "pose" relates to a spatial arrangement of the imaging arrangement in relation to a subject to be imaged. The term pose thus relates to a spatial identification. The term "pose" relates to a subject's posture, i.e. arrangement of the movable body parts or segments to each other like a closed or opened jaw, and to a geometric arrangement of an X-ray source and an X-ray detector to each other and in relation to a subject.

In an example, the matching pose of 3D data corresponding to the 2D live image is determined from the 3D reconstructed data and the live image. In an example, this is provided as an example of a 3D-2D registration, with the possible constraint that this operation may ignore the presence of injected structures (vessels) in one or the other data source (usually in the 2D live data).

For pose estimation, numerous computer vision or machine-learning methods are provided to solve this task. In an example, the reconstruction operation is adapted and external radio-opaque markers implanted on the patient are used to make this operation faster or more robust. For example, markers are present in both the 3D and the 2D live data, and a geometrical transform matching their projections from 3D to their life locations in 2D determines the targeted pose.

In an example of the device, not shown in detail, for finding a matching pose the data processor 14 is configured to provide at least one of the group of: i) a pose estimation that is based on a system-based geometric registration; ii) a segmentation-based pose estimation; iii) a constraint that the presence of contrast injected vascular structures is ignored in the 2D live X-ray image and/or in the 3D image data; and iv) a generation of a plurality of digitally reconstructed radiographies for different projection directions of the 3D image data and use of the plurality of digitally reconstructed radiographies for identification of possible matching with the 2D live image.

The contrast injected vascular structures represent the vessels.

In an example, for the matching pose, radio-opaque markers are provided attached to the subject, which markers are present in both the 3D image data and the 2D live X-ray image. A geometrical transform that is matching their projections from 3D to their locations in 2D determines the targeted pose.

In an example, the external radio-opaque markers are temporarily implanted on the subject.

In an example, an image-based registration is provided.

In an example, the registering of the 3D image data and the 2D live image is provided dependent of the target anatomy. For rigid anatomic structures, a rigid transformation is provided. For non-rigid structures, an elastic deformation is provided.

In an example, the 3D image data is provided as at least two different sub-volumes. The sub-volumes are adjustable in their spatial orientation relative to each other.

For example, for compensating jaw motion of a subject, a respective sub-volume is identified that can then be articulated in the 3D data.

In an example of the device, not shown in detail, for the mask generating, the data processor 14 is configured to invert the transfer function of the 3D reconstruction plus projection process. In other words, an inverse of the transfer function of the "3D reconstruction+projection" process is provided. This has the effect that re-projections are provided matching as good as possible the live images.

For example, both radiometry and the full spatial spectrum are adapted.

In addition, this should occur on a spatially varying basis. Blind or informed deconvolution/restoration techniques are provided to achieve that goal.

In an example of the device, not shown in detail, the data processor 14 is configured to provide a 2D scatter estimation using the 2D live X-ray image as input or a 3D scatter estimation.

The data processor 14 is configured to add a scatter signal to the computed digitally reconstructed radiography.

This provides the effect that it may contain scattering structures that are not in the field of view of the 3D reconstructed image, e.g. the patient table.

This provides further improvements that can make the DRR and the angiography more consistent.

In an example, the 2D scatter estimation is using the angiographic image as input.

In an example of the device, not shown in detail, as correction for the reconstruction of the 3D image data, the data processor 14 is configured to provide i) a virtual heel effect correction. In addition or alternatively, the data processor 14 is configured to provide ii) a virtual inverse detector gain correction.

The heel effect correction and detector gain correction are used to create virtually a homogeneous X-ray intensity. Due to the heel effect, the emission intensity of X-rays is slightly different for every emission angle. The detector X-ray detection efficiency varies for every pixel, due to various factors like the internal detector composition. In the 2D live data, these effects may or may not be corrected. Furthermore, if a correction is applied the correction may be a simplification of the real effect, and thus not fully accurate. For the DRR generation these correction steps can be inversely applied if no correction is used on the 2D live data. Thus, in the DRR a virtual inhomogeneity can be created similar to the 2D live data. Alternatively, the heel effect and detector gain can be taken into account during DRR generation simulating the physical reality of the system, and then the simplified correction of the 2D live data is applied in order to achieve the same correction with limited accuracy is created on the DRR.

In an example, for both effects, calibration data from the image reconstruction pipeline is used.

In an example, if the digitally reconstructed radiography, after restoration, is not geometrically matching the live image, a 2D registration process may be provided. As an example, at least a part of out-of-plane motions are corrected by the adapting steps. The subsequent 2D registration process can thus produce good results, even in the presence of harsh patient movements. Subtraction can then be applied, producing a clean and improved digital subtraction angiography.

Referring back to FIG. 3, in an example of the method, not shown in detail, for achieving the adapted 2D mask image, the following steps are provided:

receiving the projection data of the region of interest comprising the plurality of the 2D projection images;

receiving 2D data characteristics from an acquisition of the 2D live X-ray image; and adapting, based on the 2D data characteristics, the reconstruction of the projection data of the region of interest to generate adapted 3D image data that comprises an adapted 3D representation of the object. The adapted 3D image data is used for the computation of the digitally reconstructed radiography.

In an option, the adapted 3D image data is also used for the registration.

In an example of the method, for achieving the adapted 2D mask image, the following steps are provided:

receiving 2D data characteristics from an acquisition of the 2D live X-ray image; and adapting, based on the 2D data characteristics, the computation of the digitally reconstructed radiography from the 3D image data to generate an adapted 2D mask image.

In an example, the 2D data characteristics are based on i) 2D live acquisition parameters comprising at least one of the group of spectrum, resolution and X-ray imaging energy. In addition or alternatively, the 2D data characteristics are based on ii) image data of the 2D live X-ray image comprising at least one of the group of resolution and contrast.

In an example of the method, for the 3D image data, the adapted reconstruction comprises reconstructed attenuation values that correspond to a predetermined mean photon energy that is expected to be used for the 2D live X-ray image.

In an option of the method, the 3D image is segmented into bone and soft tissue type regions so that each tissue type has individually adjusted attenuation values for the expected photon energy. In another option, for the digitally reconstructed radiography different spectrum-related factors are applied. In a further option, the 3D image data is vessel-les In an example of the method, it is provided the step of estimating a pose of the object in the 2D live X-ray image. Further, i) for the registration of the 3D image data and the 2D live X-ray image, the 3D representation of the object of the 3D image data is aligned to the estimated pose. In addition or alternatively, ii) for the reconstruction of the projection data of the region of interest, the estimated pose is considered for the reconstruction.

In an example of the method, for finding a matching pose it is provided at least one of the group of:

i) a pose estimation that is based on a system-based geometric registration;

ii) a segmentation-based pose estimation;

iii) a constraint that the presence of contrast injected vascular structures is ignored in the 2D live X-ray image and/or in the 3D image data; and iv) generating a plurality of digitally reconstructed radiographies for different projection directions of the 3D image data and using the plurality of digitally reconstructed radiographies for identifying possible matching with the 2D live image.

In an example of the method, for the mask generating, the transfer function of the 3D reconstruction plus projection process is inverted.

In an example of the method, a 2D scatter estimating is provided using the 2D live X-ray image, for example the angiographic image, as input. In another example, a 3D scatter estimating is provided. A scatter signal is added to the computed digitally reconstructed radiography.

In an example of the method, as correction for the reconstruction of the 3D image data, it is provided i) a virtual heel effect correction and/or ii) a virtual inverse detector gain correction.

Figure 4:
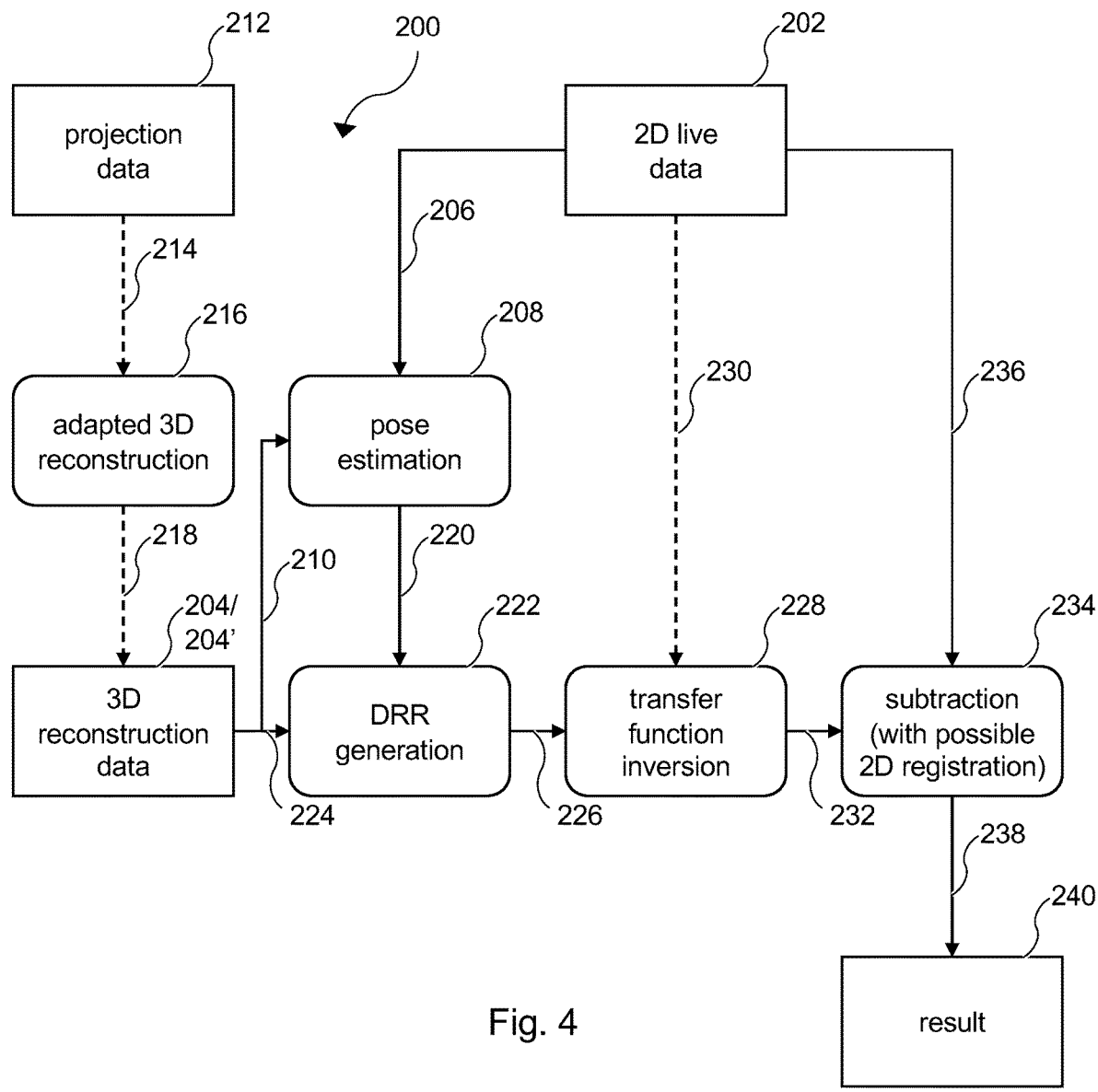
FIG. 4 shows an example of a workflow for digital subtraction imaging.

FIG. 4 shows an example of a workflow 200 for digital subtraction imaging. As a start so-to-speak, 2D live data 202 and 3D reconstruction data 204 is provided. The 2D live data 202 is used 206 for a pose estimation procedure 208. The 3D reconstruction data 204 is also used 210 for the pose estimation procedure 208.

As an option, indicated by dotted lines, projection data 212 is provided and used 214 for an adapted 3D reconstruction procedure 216 leading 218 to adapted 3D reconstruction data 204'. The pose estimation procedure 208 is connected 220 to a DRR generation 222 that also receives 224 an input from the 3D reconstruction data 204 or the adapted 3D reconstruction data 204'. The DRR generation 222 is connected 226 to a transfer function inversion procedure 228.

As an option, indicated by a dotted line, the 2D live data 202 is also supplied 230 to the transfer function inversion procedure 228.

The transfer function inversion procedure 228 is connected 232 to a subtraction procedure 234 with a possible 2D registration, for which procedure also the 2D live data 202 is also provided 236. As an outcome of the subtraction procedure 234 with a possible 2D registration, it is provided 238 a result 240, for example displayed as subtraction image, i.e. an adapted subtraction image.

Figure 5:
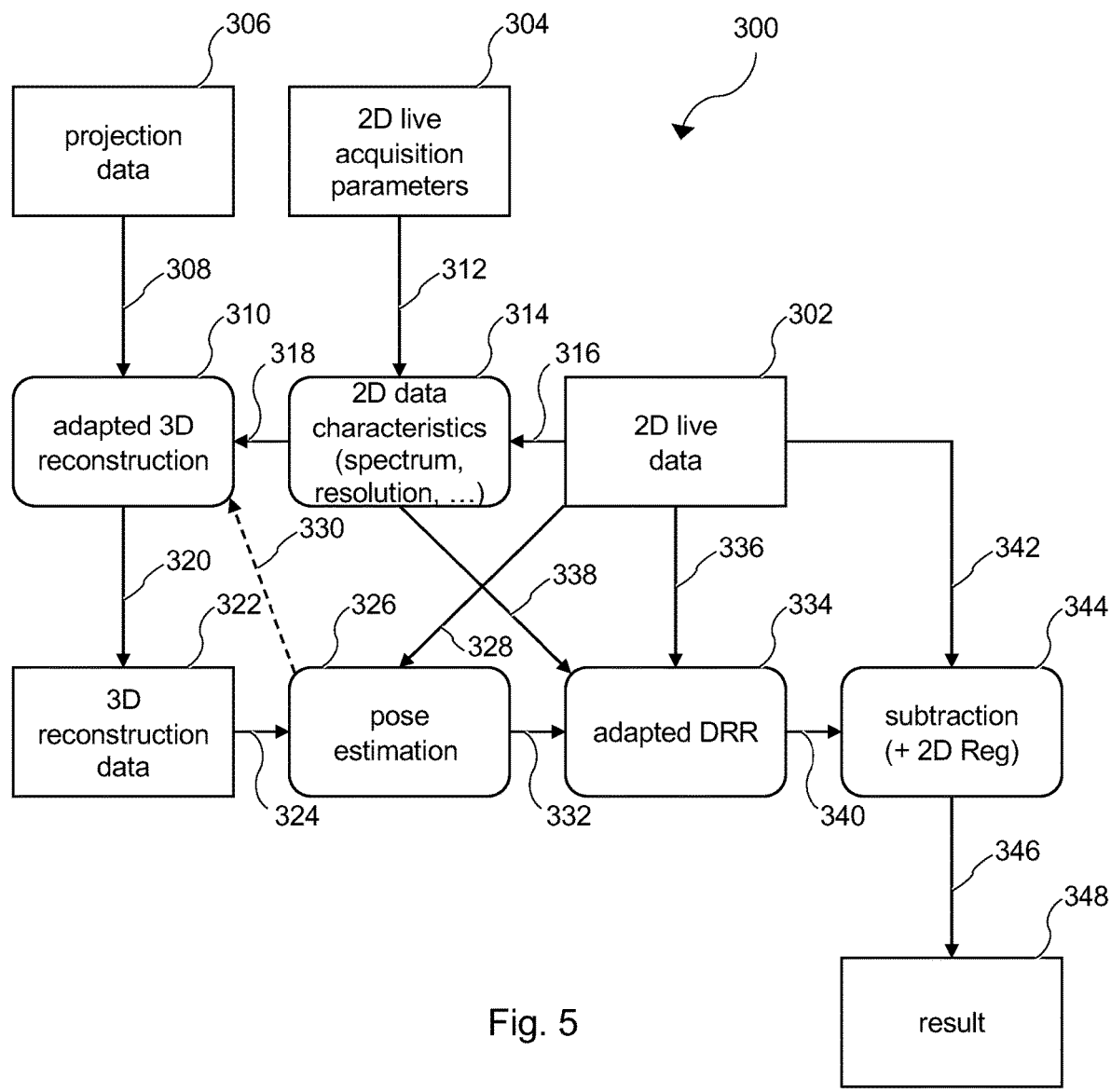
FIG. 5 shows another example of a workflow for digital subtraction imaging.

FIG. 5 shows another example of a workflow 300 for digital subtraction imaging. As a start so-to-speak, 2D live data 302, 2D live acquisition parameters 304 and projection data 306 are provided. The projection data 306 is used 308 in an adapted 3D reconstruction procedure 310. The 2D live acquisition parameters 304 are provided 312 to a 2D data characteristics determination procedure 314 providing data like spectrum, resolution and the like, which 2D data characteristics determination procedure 314 also receives 316 the 2D live data 302. The 2D data characteristics determination procedure 314 is connected 318 to the adapted 3D reconstruction procedure 310. The adapted 3D reconstruction procedure 310 leads 320 to 3D reconstruction data 322 that is supplied 324 to a pose estimation procedure 326. The pose estimation procedure 326 also receives 328 the 2D live data 302.

As an option, indicated by a dotted line, the pose estimation procedure is connected 330 back to the adapted 3D reconstruction procedure 310, providing a loop like procedure for optimization in determining the pose. The connecting arrow 330 from pose estimation 326 towards the 3D reconstruction 310 indicates that the adaptation of 3D reconstruction to live data could be refined once the pose is known. In that case, not only the live data characteristics but also the actual live data content could drive the adaption process. In an example, an iterative reconstruction method is used with the registered live data as additional input. Reconstruction parameters are iteratively optimized to maximize the resemblance of a DRR with the registered live data. For example, a root mean square difference on selected regions of the live data is used to measure this resemblance.

The pose estimation procedure 326 is further connected 332 to an adapted DRR procedure 334 that receives 336 the 2D live data 302 and that is also connected 338 to the 2D data characteristics determination procedure 314. The adapted DRR procedure 334 is connected 340 to a subtraction plus 2D registration procedure 344, which also receives 342 the 2D live data 302. As an outcome of the subtraction plus 2D registration procedure 344, it is provided 346 a result 348, for example displayed as subtraction image, i.e. an adapted subtraction image.

It is noted that in FIG. 4 and FIG. 5, square-corner rectangles represent data and rounded-corner rectangles stand for procedures, i.e. processing steps or data gathering/providing steps. The arrows represent the application of a processing step on input data to produce output data. The dashed arrows represent the optional application of a processing step on input data to produce output data.

It is further noted that in FIG. 5, the frames 310, 314 and 334 are basically providing the different adaptation options. The frames 306 and 322 pertain to the 3D context, whereas the frames 304 and 302 are related to the live 2D context.

In another example, a computer program is provided that comprises a computer readable code or instructions which when executed by a processor enable the processor to carry out the method of one of the preceding examples, for example on an appropriate system.

In an example, a computer program or program element for controlling an apparatus according to one of the examples above is provided, which program or program element, when being executed by a processing unit, is adapted to perform the method steps of one of the method examples above.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

In another example to be claimed, a computer readable medium having stored the computer program of the preceding example.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for digital subtraction imaging, the device comprising:
    a processor configured to
    receive 3D image data of a region of interest of an object, wherein the 3D image data comprises a 3D representation of the object that is based on a reconstruction from a plurality of 2D projection images of the region of interest;
    receive a 2D live X-ray image of the region of interest;
    register the 3D image data and the 2D live X-ray image, wherein a matching pose of the 3D image data corresponding to the 2D live X-ray image is determined to compute a digitally reconstructed radiography from the 3D image data based on the determined matching pose to generate a 2D mask image and to use, for the generating of the 2D mask image, current data related to the 2D live X-ray image to achieve an adapted 2D mask image, wherein the data related to the 2D live X-ray image comprises at least one of 2D live acquisition parameters or data of the 2D live X-ray image;
    subtract the generated adapted 2D mask image from the 2D live X-ray image; and
    provide a digital image highlighting changes in the region of interest.

2. The device according to claim 1, wherein the image data input is configured to receive an angiographic contrast injected 2D live X-ray image of the region of interest as the 2D live X-ray image;
    wherein the processor is configured to subtract the generated adapted 2D mask image from the angiographic contrast injected 2D live X-ray image; and
    wherein the processor is configured to provide a digital subtraction angiography representing a vascular structure in the region of interest.

3. The device according to claim 1, wherein, for achieving the adapted 2D mask image:
    the processor is configured to receive the projection data of the region of interest comprising the plurality of the 2D projection images; and to receive 2D data characteristics from an acquisition of the 2D live X-ray image;
    the processor is configured to adapt, based on the 2D data characteristics, the reconstruction of the projection data of the region of interest to generate adapted 3D image data that comprises an adapted 3D representation of the object;
    the processor is configured to use the adapted 3D image data for the computation of the digitally reconstructed radiography; and
    the processor is configured to use the adapted 3D image data also for the registration.

4. The device according to claim 1, wherein, for achieving the adapted 2D mask image:
    the processor is configured to receive 2D data characteristics from an acquisition of the 2D live X-ray image; and the processor is configured to adapt, based on the 2D data characteristics, the computation of the digitally reconstructed radiography from the 3D image data to generate an adapted 2D mask image.

5. The device according to claim 1, wherein the 2D data characteristics are based on at least one of:
   i) 2D live acquisition parameters comprising at least one of the group of: spectrum, resolution and X-ray imaging energy; or
   ii) image data of the 2D live X-ray image comprising at least one of the group of: resolution and contrast.

6. The device according to claim 1, wherein, for the 3D image data, the adapted reconstruction comprises reconstructed attenuation values that correspond to a predetermined mean photon energy that is expected to be used for the 2D live X-ray image; and
   wherein the processor is configured to segment the 3D image segmented into bone and soft tissue type regions so that each tissue type has individually adjusted attenuation values for the expected photon energy; and
   wherein the processor is configured to apply different spectrum-related factors for the digitally reconstructed radiography; and
   wherein the 3D image data is vessel-les.

7. The device according to claim 1, wherein the processor is configured to estimate a pose of the object in the 2D live X-ray image; and
   wherein at least one of:
   i) for the registration of the 3D image data and the 2D live X-ray image, the processor is configured to align the 3D representation of the object of the 3D image data to the estimated pose; or
   ii) for the reconstruction of the projection data of the region of interest, the processor is configured to consider the estimated pose for the reconstruction.

8. The device according to claim 1, wherein, for finding a matching pose the is configured to provide at least one of of:
   i) a pose estimation that is based on a system-based geometric registration;
   ii) a segmentation-based pose estimation;
   iii) a constraint that the presence of contrast injected vascular structures is ignored in at least one of the 2D live X-ray image or in the 3D image data; and or
   iv) generation of a plurality of digitally reconstructed radiographies for different projection directions of the 3D image data and use of the plurality of digitally reconstructed radiographies for identification of possible matching with the 2D live image.

9. The device according to claim 1, wherein, for the mask generating, the processor is configured to invert the transfer function of the 3D reconstruction plus projection process.

10. The device according to claim 1, wherein the processor is configured to provide:
    a 2D scatter estimation using the 2D live X-ray image as input; or
    a 3D scatter estimation; and
    wherein the processor is configured to add a scatter signal to the computed digitally reconstructed radiography.

11. The device according to claim 1, wherein, as correction for the reconstruction of the 3D image data, the processor is configured to provide at least one of:
    i) a virtual heel effect correction; or
    ii) a virtual inverse detector gain correction.

12. The device according to claim 1, further comprising:
    a display
    configured to present the digital representing the vascular structure in the region of interest.

13. An imaging system for digital subtraction imaging, the system comprising:
    an X-ray imaging device with an X-ray source and an X-ray detector; and
    a device for digital subtraction imaging according to claim 1;
    wherein the X-ray imaging device is configured to generate the 2D live X-ray image.

14. A method for digital subtraction imaging, the method comprising:
    receiving 3D image data of a region of interest of an object, wherein the 3D image data comprises a 3D representation of the object that is based on a reconstruction from a plurality of 2D projection images of the region of interest;
    receiving a 2D live X-ray image of the region of interest;
    registering the 3D image data and the 2D live X-ray image, wherein a matching pose of the 3D image data corresponding to the 2D live X-ray image is determined;
    computing a digitally reconstructed radiography from the 3D image data based on the determined matching pose to generate a 2D mask image; wherein, for the generating of the 2D mask image, current data related to the 2D live X-ray image is used to achieve an adapted 2D mask image, wherein the data related to the 2D live X-ray image comprises at least one of the group of 2D live acquisition parameters and data of the 2D live X-ray image;
    subtracting the generated adapted 2D mask image from the 2D live X-ray image; and
    providing a digital image highlighting changes in the region of interest.

15. A non-transitory computer-readable storage medium having stored a computer program instructions which, when executed by a processor, cause the processor to;
    receive 3D image data of a region of interest of an object, wherein the 3D image data comprises a 3D representation of the object that is based on a reconstruction from a plurality of 2D projection images of the region of interest;
    receive a 2D live X-ray image of the region of interest;
    register the 3D image data and the 2D live X-ray image, wherein a matching pose of the 3D image data corresponding to the 2D live X-ray image is determined;
    compute a digitally reconstructed radiography from the 3D image data based on the determined matching pose to generate a 2D mask image; wherein, for the generating of the 2D mask image, current data related to the 2D live X-ray image is used to achieve an adapted 2D mask image, wherein the data related to the 2D live X-ray image comprises at least one of the group of 2D live acquisition parameters and data of the 2D live X-ray image;
    subtract the generated adapted 2D mask image from the 2D live X-ray image; and
    provide a digital image highlighting changes in the region of interest.

* * * * *